(12) United States Patent
Thomas et al.

(10) Patent No.: US 6,427,522 B1
(45) Date of Patent: Aug. 6, 2002

(54) FAST TEMPERATURE PROGRAMMED GAS CHROMATOGRAPH

(75) Inventors: Thomas J. Thomas, Lewisburg; Ronnie D. Bennett, Ronceverte, both of WV (US)

(73) Assignee: ABB Automation Inc., Wickliffe, OH (US)

( * ) Notice: Subject to any disclaimer, the term of this patent is extended or adjusted under 35 U.S.C. 154(b) by 0 days.

(21) Appl. No.: 09/780,730

(22) Filed: Feb. 9, 2001

(51) Int. Cl.[7] .......................... G01N 30/02; B01D 53/02
(52) U.S. Cl. .......................................... 73/23.35; 95/87
(58) Field of Search .............................. 73/23.35, 23.39; 95/87; 96/101

(56) References Cited

U.S. PATENT DOCUMENTS

| | | |
|---|---|---|
| 4,726,822 A | 2/1988 | Cates et al. |
| 5,028,243 A | 7/1991 | Rubey ........................... 95/87 |
| 5,215,556 A | 6/1993 | Hiller et al. ................... 95/87 |
| 5,589,630 A | 12/1996 | Wiegand et al. |
| 5,808,178 A | 9/1998 | Rounbehler et al. ....... 73/23.39 |
| 6,209,386 B1 | 4/2001 | Mustacich et al. ......... 73/23.39 |

Primary Examiner—Hezron Williams
Assistant Examiner—Jay L Politzer
(74) Attorney, Agent, or Firm—Michael M. Rickin

(57) ABSTRACT

A temperature programmed module for use in a gas chromatograph. The module has micropacked column and inner and outer jacket tubes. The inner jacket tube surrounds the column to provide a space between the that tube and the column. The outer jacket tube surrounds the inner jacket tube to provide a space between the two jacket tubes. Air which has a controlled temperature flows only in the space between the two jacket tubes when it is desired to heat the column. Air flows in both spaces when it is not desired to heat the column. The temperature of the air is controlled. The module along with the sample injection valve and flame ionization detector are in an enclosure that is not temperature controlled. The air that flows in both spaces also flows in the enclosure to keep the heat from the valve and the flame ionization detector from heating the column.

35 Claims, 8 Drawing Sheets

FAST TEMPERATURE PROGRAMMED GAS CHROMATOGRAPH

FIELD OF THE INVENTION

This invention relates to gas chromatographs (GCs) and more particularly to a temperature programmed GC that has a shorter time required for heating and cooling of the GC column.

DESCRIPTION OF THE PRIOR ART

Temperature programmed GCs are typically used in process applications for two reasons. The first is to provide faster analysis times for long, complex analyses. These applications are traditionally developed from laboratory techniques, where temperature programming is used routinely to speed the elution time. In this instance, the laboratory analysis is merely "dropped" into the analyzer.

The second category of applications are those where the temperature programming is used to influence the desired elution. In this category are distillation analyses of mixtures with a broad boiling point range. The application of heat to these columns causes a shift in equilibrium between the gas and the liquid phase toward the gas phase which in turn causes the components to elute from the columns in a more complete and timely manner.

None of the foregoing applications are known for their speed. In some cases, the slowness of the application precludes the use of an analyzer in the control loop, relegating the analyzer to be used in an advisory capacity to the control algorithm. Therefore, the applications using these analyzers are not typically run near their limits, nor are they necessarily optimized for maximum revenue by the refiner or chemical producer.

Efforts have been made in the past to speed up the analysis times of GCs. Initial efforts were concentrated in studying the fundamentals of the partitioning process in the GC column. For example, B. O. Ayers and D. D. DeFord in "High Speed Process Gas Chromatograph," Analytical Chemistry, 32, p 698, (1960) describe the design constraints necessary to optimize operational parameters of chromatographs to the point where a group of six hydrocarbons can be analyzed in 25 seconds.

The heart of a GC system is the column. Column performance sets limits to the separations attainable and helps determine the speed of analysis. Three basic types of columns are used in gas chromatography.

The first type of column are conventionally packed columns which have been used since the introduction of gas chromatography by A. T. James and A. J. P. Martin in 1952. By 1960, R. J. Loyd et al. reported in "Optimization of Resolution—Time Ratio with Packed Chromatographic Columns," Analytical Chemistry, Volume 32, Number 6, p 698 a ninefold improvement in the time required to obtain a given chromatographic separation using columns containing a low proportion of partitioning agent and a carrier gas of low viscosity and high diffusivity.

Other parameters which affect the resolution and speed of packed columns such as liquid loading, solid support characteristics, column diameter and length have been investigated and reported in numerous articles and presentations.

The second type of column is the micropacked column which is a packed column with an internal diameter of 0.5 to 1 mm and the same packing density as a conventional packed column. Micropacked columns have been used in gas chromatography since 1963. Because of the advantages micropacked columns possess, numerous process applications have been done using this column type. The advantages include reproducibility, a small carrier gas flow rate and high efficiency. Supports may be coated with any stationary phase in the desired quantity. The column packing may be prepared in large batches to ensure reproducible properties. The pressure drop is not excessive while the number of theoretical plates per unit length is high. The major problem associated with this type of column is difficulty in packing longer lengths (>10 feet). These columns are normally packed in $\frac{1}{16}$ inch stainless tubing and it is visually impossible to determine if there are empty spaces within the column.

The third type of column is the capillary (0.1 to 1.0 mm I.D.) or wall coated open tubular (WCOT) columns introduced by Golay in 1957. Numerous articles have been written and extensive research has been conducted to define the benefits of capillary columns in process gas chromatography for resolution and speed of analysis which these columns provide. Parameters such as column diameter/length, stationary film thickness, column material, and carrier flows/pressures have been studied and optimized for reduced analysis time in process applications. The wide-bore capillary has been of particular interest for process applications because it can be used as a direct replacement for a packed column without changing operating parameters or sample preparation. The associated benefit is a dramatic decrease in analysis time without changing sample size.

Another unique approach to providing faster analysis times without sacrificing sensitivity and requiring small sample volumes is the multicapillary column. This column was introduced by Alltech in the late 1990's by combining over 900 liquid phase coated, 40 $\mu$m capillaries in a single glass tube. Compared to conventional capillary columns, multicapillary columns maintain high efficiency across a broader flow rate range, operate at lower temperatures and provide faster analyses.

Although numerous advances have been made relative to speed of analysis by manipulating the column types and parameters, there is a theoretical limit to what can be done to decrease time for the sample to reach equilibrium between the mobile and stationary phases. Or more precisely, reduce analysis time without sacrificing separation.

Two of the factors, that affect this equilibrium time, are temperature and carrier gas pressure/flow. By increasing either or both of these parameters there will be a decrease in analysis time.

Temperature programming which is a controlled change in the temperature surrounding the column has been used to speed up the analysis time of wide boiling range samples since the early 1960's [see for example A. J. Martin, "Linear Programmed Temperature Gas Chromatography to 500° C.," Edinburgh Symposium, London, Butterworths, 208–10 (1960)]. The most common application is the use of temperature programming for simulated distillation of fuel products. By increasing the temperature, the time spent by a sample in the liquid phase is decreased which shifts the equilibrium to the gas phase which reduces the time of analysis. One point to be considered with temperature programming is cycle times, which is the length of time from sample inject for one analysis to sample inject for the next analysis and includes cool down time. Although the analysis time may have. been significantly reduced by temperature programming, the consideration of the time it takes to cool down to the initial temperature diminishes the benefit gained. Regardless, this approach has been used to reduce the analysis time for many complex process samples and would have greater benefit if the heating and cooling cycles can be reduced.

Pressure/flow programming of the carrier gas has more recently become available on process gas chromatographs and can also be used to reduce analysis times. By increasing the pressure/flow in a controlled manner the time for the sample to reach equilibrium is reduced and the sample is swept through the column to the detector by the faster flow of the carrier gas. Pressure/flow can be used independently of temperature or both can be used simultaneously to speed the analysis. There is a special benefit to using pressure programming when the liquid phase in the column has reached its maximum operating temperature.

In the mid to late 1980's the microchip gas chromatograph, also known as the "GC on a chip", was developed and introduced by Microsensor Technology, Fremont, Calif. The major benefit associated with this development was speed of analysis which was gained through miniaturization of each of the chromatographic components, including the column which was etched on a silicon wafer. Factors such as no backflush, no liquid inject, limited column/detector choices, and lack of temperature control have limited the use of this technology to speed up applications, although recently some of the limitations have been resolved.

Another approach to speeding up of analysis cycle times has recently been introduced by Applied Automation, Inc. using a technique known as parallel chromatography. This approach has been made possible by the availability of powerful, inexpensive computerized electronic controllers. The time for the analysis to be completed is dependent on the sample train with the longest analysis time.

As was discussed above, if temperature programming of the column could be done faster from both a heating and cooling perspective, there would be significant benefits to be gained for faster process gas chromatographic analysis. This fact was recognized very early in the evolution of the technology, when in 1961 and 1963, Perkin-Elmer introduced laboratory chromatographs which used resistive or direct heating of the chromatographic column. The column is its own heating element. A low voltage, high amperage current is passed through the column, which becomes heated by resistance heating.

U.S. Pat. No. 4,726,822 describes the use of a fast response thermochromatographic capillary column which has a thin coating of a metallic compound applied to the outer surface. When a current is passed through the column it heats and cools very quickly.

Thermedics Detection, Inc., Chelmsford, Mass. has developed a very fast temperature programming technique using resistive heating of a fused silica capillary column contained within a metal tube. A current is passed through the outer tube heating the column to temperatures up to 1200° C./min. The combination of a short column (5 m×0.25 mm I.D.), a high gas flow rate (up to 10 ml/min), and fast temperature programs typically decreased analysis times from 30 minutes to about 2.5 minutes. C. Rankin and R. Sacks have reported in "A Computer-Controlled, High Speed, Repetitive Gas Chromatography System," LC-GC, Volume 9, Number 6, pp 428–434, (1991) the use of a gas cooled and electrically heated metal capillary tube as a cryofocusing inlet system, and a vacuum pump for backflushing high boilers as a means to accomplish analysis cycle times in the 10–20 second range.

RVM Scientific, Inc., uses resistive heating wires wrapped around the capillary column. The wire wrapped capillary is insulated using a proprietary technique to ensure rapid and stable temperature control.

U.S. Pat. No. 5,589,630 describes a fast GC that employs low dead volume fittings, high speed injectors and detectors, a fast temperature program module, and a high speed data acquisition system. The fast temperature programming module can rapidly heat and cool the column as required to achieve analysis of compounds whose boiling points differ by as much as 250° C. in less than two minutes, possibly in less than one minute. The fast temperature module described therein has a heating means that is preferably electrical resistance or an induction heater and uses the flow of unheated heat transfer fluid. for cooling the column.

SUMMARY OF THE INVENTION

A temperature programmed module for use in a gas chromatograph that has a micropacked column through which a current can be passed to heat the column. The module also has an inner jacket tube surrounding the column and having an outer diameter greater than the outer diameter of the column to define a space between the between the first jacket tube and the column. The module further has an outer jacket tube surrounding the inner jacket tube and having an outer diameter greater than the inner jacket tube outer diameter to define a space between the outer and the inner jacket tubes. Air having a controlled temperature flowing only into the space between the outer and the inner jacket tubes when it is desired to heat the column by passing the current through the column.

In a gas chromatograph, an enclosure whose temperature is not controlled. The enclosure has a temperature programmed module. The module has a micropacked column through which a current can be passed to heat the column. The module also has an inner jacket tube surrounding the column and having an outer diameter greater than the outer diameter of the column to define a space between the between the inner jacket tube and the column. The module further has an outer jacket tube surrounding the inner jacket tube and having an outer diameter greater than the inner jacket tube outer diameter to define a space between the outer and the inner jacket tubes. Air having a controlled temperature flowing only into the space between the outer and the inner jacket tubes when it is desired to heat the column by passing the current through the column.

A method for assembling a temperature module having a micropacked column. The method has the steps of:

(a) surrounding the column with a first jacket tube having an outer diameter greater than the outer diameter of the column to define a space between the first jacket tube and the column;

(b) surrounding the first jacket tube with a second jacket tube having an outer diameter greater than the first jacket tube outer diameter to define a space between the first and the second jacket tubes; and (c) providing on the outer surface of the first jacket tube prior to surrounding that tube with the second jacket tube a means for centering the first jacket tube in the second jacket tube.

A method for using a temperature module having a micropacked column through which a current can be passed to heat the column. The column is surrounded by an inner jacket tube having an outer diameter which is greater than the outer diameter of the column to define a space between the column and the inner jacket tube and an outer jacket surrounding the inner jacket tube the outer jacket having an outer diameter greater than the inner jacket tube outer diameter to define a space between the outer and the inner jacket tubes. The method has the step of flowing air having a controlled temperature only into the space between the outer and the inner jacket tubes when it is desired to heat the column by passing the current through the column.

A gas chromatograph comprising:

(a) a sample injector valve;

(b) a flame ionization detector; and (c) a temperature programmed module connected between said sample injector valve and the flame ionization detector, the module comprising:

(i) a micropacked column through which a current can be passed to heat the column;

(ii) an inner jacket tube surrounding the column and having an outer diameter greater than the outer diameter of the column to define a space between the first jacket tube and the column; and (iii) an outer jacket tube surrounding the inner jacket tube and having an outer diameter greater than the inner jacket tube outer diameter to define a space between the outer and the inner jacket tubes;

air having a controlled temperature flowing only into the space between the outer and the inner jacket tubes when it is desired to heat the column.

DESCRIPTION OF THE PREFERRED EMBODIMENT(S)

Figure 1:
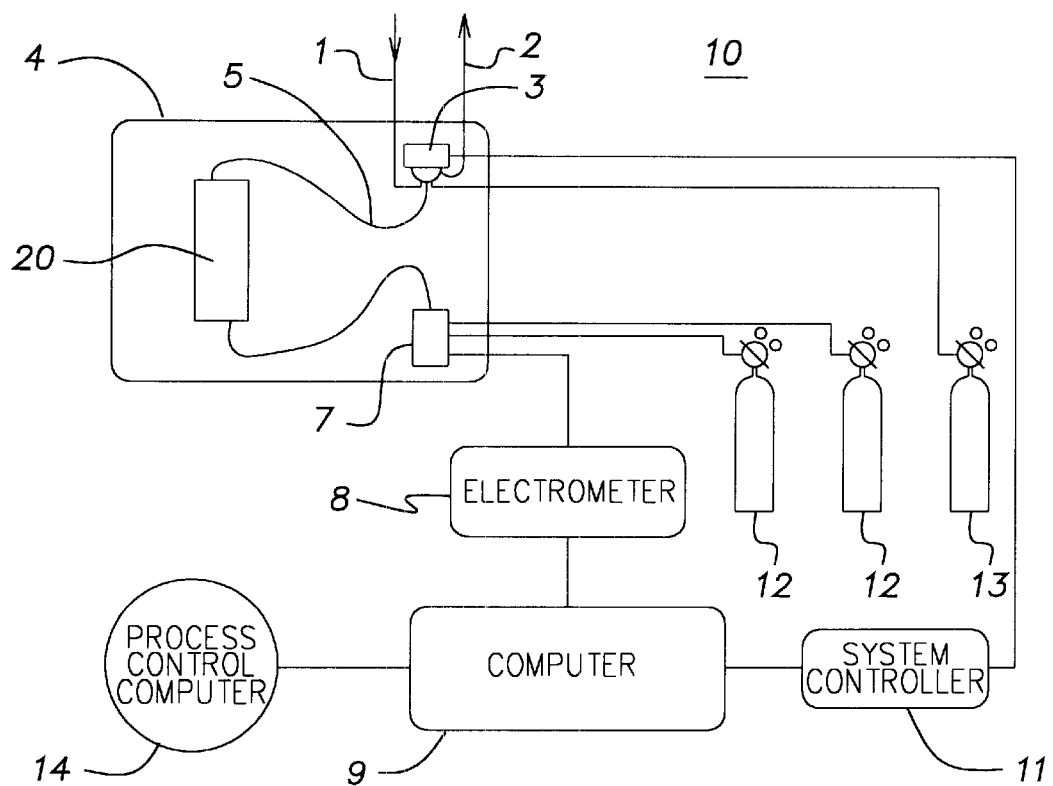
FIG. 1 shows a functional block diagram for one embodiment of the gas chromatograph that includes the temperature programmed module of the present invention.

Referring now to FIG. 1, there is shown a functional block diagram representation of one embodiment for the GC 10 that includes the temperature programmed module 20 of the present invention. The sample enters the GC 10 through conduit 1, flows through the sample injector valve 3, and exits through a vent 2. The sample is injected into the micropacked column (shown in FIG. 2) that is part of the fast temperature programming module 20. The sample flows through the chromatographic column and into the flame ionization detector 7. The injection valve 3, the micropacked column of fast temperature programming module 20 and flame ionization detector 7 are contained in an enclosure 4 which in accordance with the present invention is not temperature controlled. Fuel gases, hydrogen and air 12, are supplied to the flame ionization detector 7 and carrier gas 13 is supplied to the injection valve 3 from sources outside of the enclosure 4.

The flame ionization detector 7 produces an electrical signal which is fed to an electrometer 8. The electrometer 8 produces another electrical signal which in turn is sent to the computer 9 that contains the various analog and digital input/output boards and suitable communications boards to interface with a process control computer 14 and a system controller 11 containing an injector valve interface circuit. The process control computer 14 receives the data regarding sample component concentrations and is programmed to manipulate process variables to maintain control. of the process. A stream selector (not shown) can optionally be employed to select a particular sampling stream from multiple sources, if desired.

A flow regulation system provides a controlled flow of carrier gas and other make-up gases as required by the system to perform a separation of components in a controlled and predictable manner. The flows may be constant or varied in a preprogrammed manner. Flows may be controlled by means of flow controllers or by controlling the pressure drop across the column or other flow restricting devices.

One method for providing flow regulation is to use a conventional pressure regulator to control the column head pressure and venting the column at or near atmospheric pressure.

Figure 2:
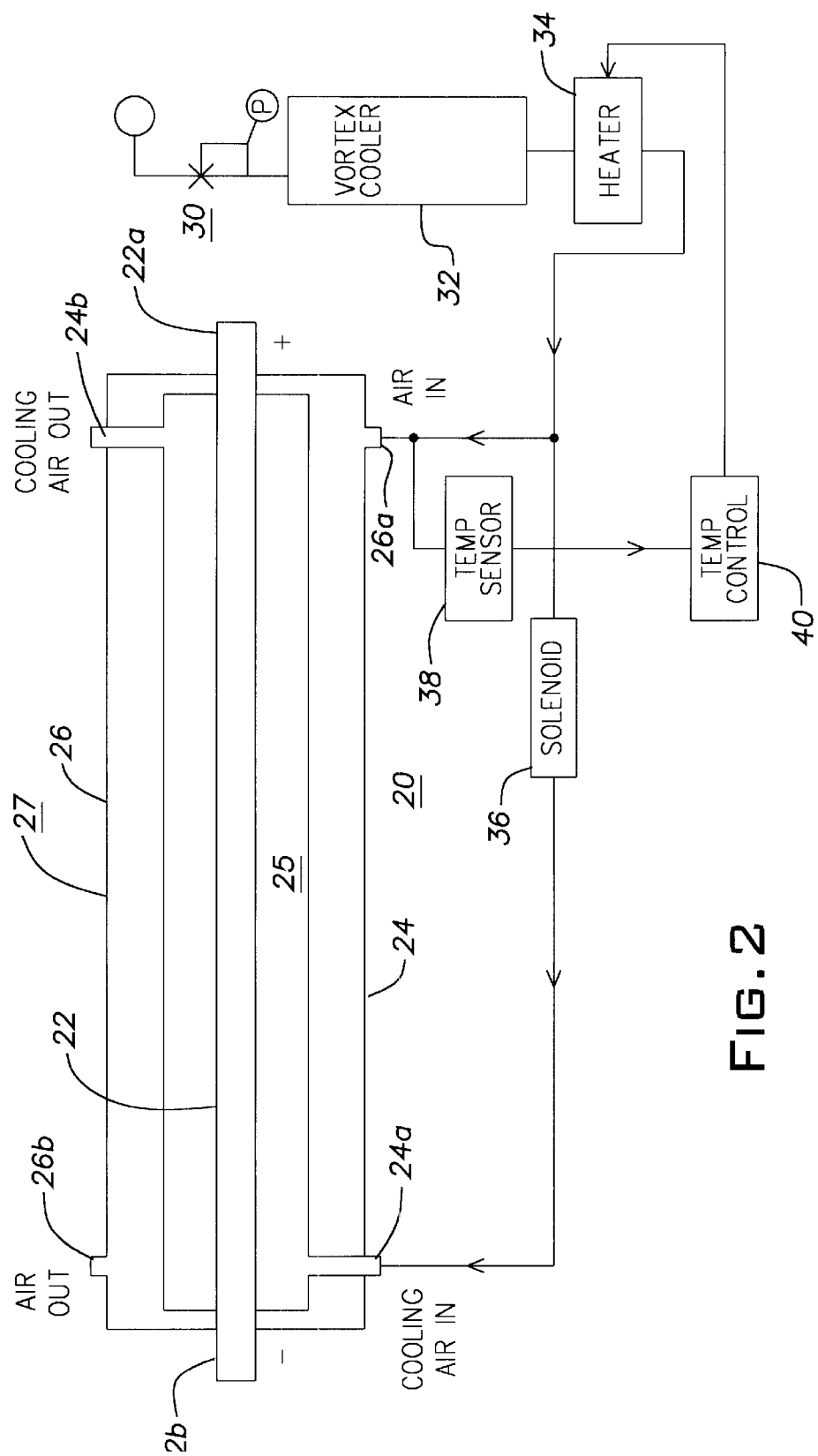
FIG. 2 shows one embodiment for the temperature programmed module.

Referring now to FIG. 2 there is shown one embodiment for the temperature programmed module 20 of the present invention and associated air supply and heating equipment. Module 20 takes advantage of direct heating of micropacked columns to speed up analysis times. As was described above, micropacked columns possess the advantages of reproducibility, a small carrier gas flow rate, and high efficiency as compared to other types of columns. In addition, micropacked columns have short lengths, low mass, and variability of packing materials available for both Gas Solid and Gas Liquid Chromatography.

The module 20 has in the embodiment shown in FIG. 2 a metal micropacked column 22 having a predetermined maximum length, inner diameter and outer diameter. The column is packed with a variety of packing materials of various mesh sizes. As is well known the packing materials are dependent on the compounds to be analyzed. A current is passed through the micropacked column 22 causing it to heat very quickly. In the present embodiment for module 20 the column went from 35° C. to 200° C. in 15 seconds.

The micropacked column 22 is concentric to first and second jacket tubes 24, 26 respectively, where both of jacket tubes 24, 26 have outer diameters greater than the outer diameter of column 22 and the outer diameter of the first jacket tube 24 is less than the outer diameter of the second jacket tube 26. There is a space 25 between first tube 24 and column 22 and a space 27 between second tube 26 and first tube 24. When the GC in which module 20 is installed is in use, air having a controlled temperature is caused to flow all of the time in the space 27 and that air is also caused to flow in space 25 except when it is desired to heat column 22.

The air is provided to module 20 from a supply (not shown in FIG. 2). The air first passes through a pressure regulator 30 and then depending on the desired temperature of the air through an optional vortex cooler 32 shown in dotted lines in FIG. 2. The air is then heated by heater 34 to a standardized temperature as it is not easy to control the temperature of the vortex cooler 32. The temperature controlled air is then provided to the "air in" input 26a of second tube 26 to thereby enter space 27. The air flows through space 27 and cools the first tube 24.

It has been found that cooling of tube 24 by the air flowing in space 27 is enhanced if a stainless steel wire (not shown in FIG. 2) is spiraled around the outer surface of tube 24. The spiral wire, which is tack welded on each revolution to the outside surface of tube 24, increases the turbulence and agitation of the air. The spiral wire also has benefits in the assembly of module 20 as will be described hereinafter. The air flowing in space 27 leaves that space through the "air out" output 26b of tube 26 and enters the enclosure 4, since as is shown in FIG. 1 module 20 is in enclosure 4.

The air from heater 34 also flows to an on/off solenoid 36 which is in the on position except when it is desired to heat column 22. When solenoid 36 is in the on position, the air flows through the solenoid 36 to the "cooling air input" 24a of tube 24 to enter space 25. The air flows through space 25 and cools the column 22. The air flowing in space 25 leaves that space through the "cooling air out" output 24b of tube 24 and enters the enclosure 4.

When solenoid 36 is in the off position, the air that would have flowed into space 25 flows into space 27. Therefore, when it is desired to heat the column all of the air flows into space 27.

As is shown in FIG. 1, the enclosure 4 also includes valve 3 and FID 7 in addition to module 20. Valve 3 and FID 7 are each individually heated and heat from these elements would reach the module 20 and cause undesirable heating of that module but for the flow of air into the enclosure from the "air out" output 26b of tube 26 and the "cooling air out" output 24b of tube 24. Thus the air exiting spaces 25 and 27 into enclosure 4 keeps the module 20 at a desired temperature. Further the exiting of air from spaces 25 and 27 into enclosure 4 provides a safety function as the plant in which the GC is used may have an explosive atmosphere.

It is desirable to keep the temperature of the air from heater 34 constant. To that end, FIG. 2 shows a temperature sensor 38 adjacent to input 26a which is used to sense the temperature of the air flowing into input 26a. The output of temperature sensor 38 is an input to a temperature controller 40. The output of controller 40 is an input to heater 34. The loop of sensor 38 and controller 40 provides the feedback to heater 34 to thereby keep the temperature of the air from heater 34 at the desired temperature.

Column 22 has first and second ends 22a and 22b to which suitable electrodes are attached. The electrodes are connected to the output of an AC power supply which provides the 10 volts that is used to heat the column.

In one embodiment of module 20, micropacked column 22 had a maximum length of 45 cm, 1 mm I.D. and 1.56 mm O.D. The column 22 was prepacked with having 100–120 and 120–140 mesh size. The first and second jacket tubes 24, 26 had outer diameters of 0.94 cm and 1.25 cm, respectively.

Figure 3:
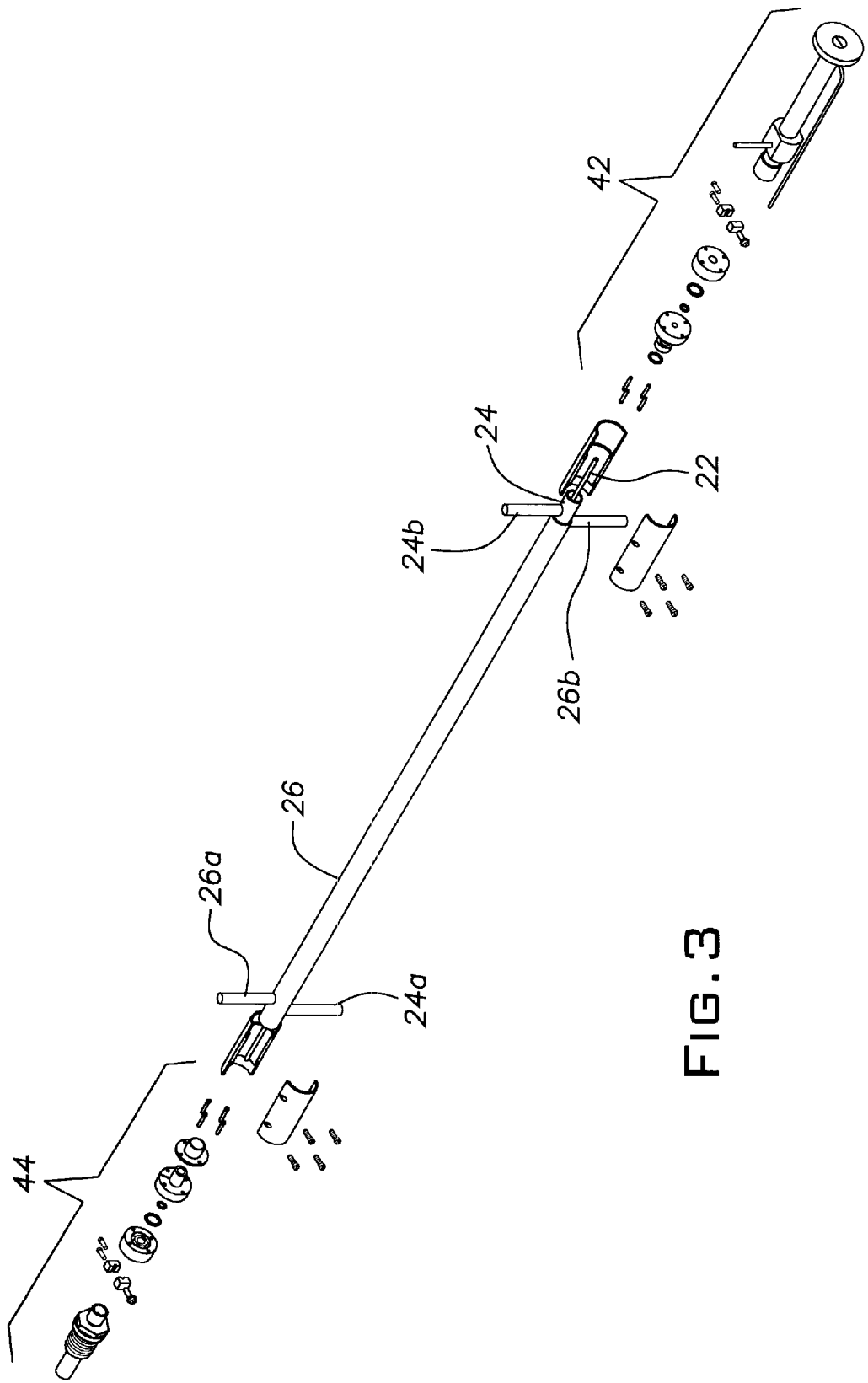
FIG. 3 the micropacked column and an exploded perspective of the hardware elements that are used to connect the temperature programmed module to the injection valve and to the flame ionization detector.
Figure 4:
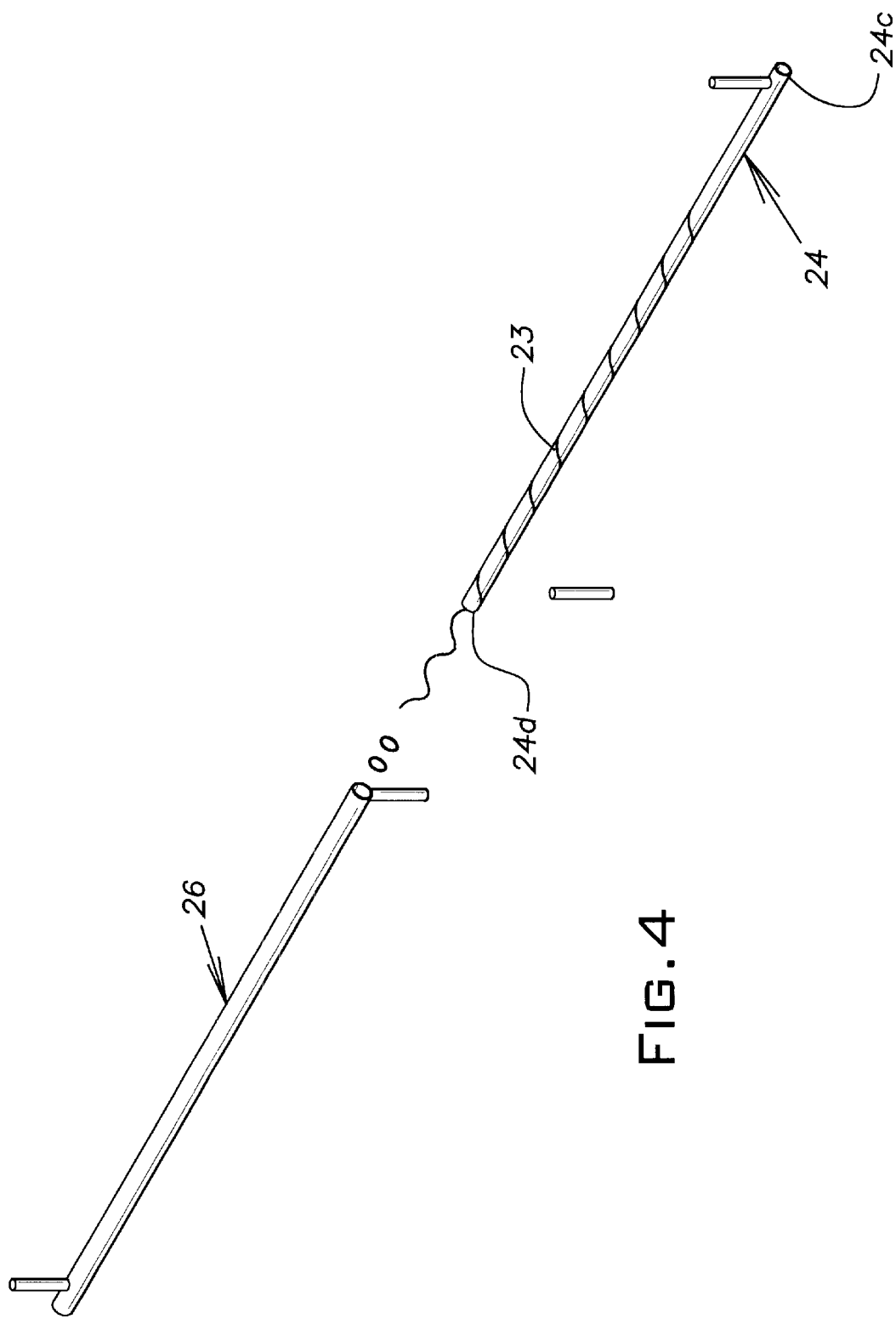
FIG. 4 shows the inner jacket of the module.
Figure 5:
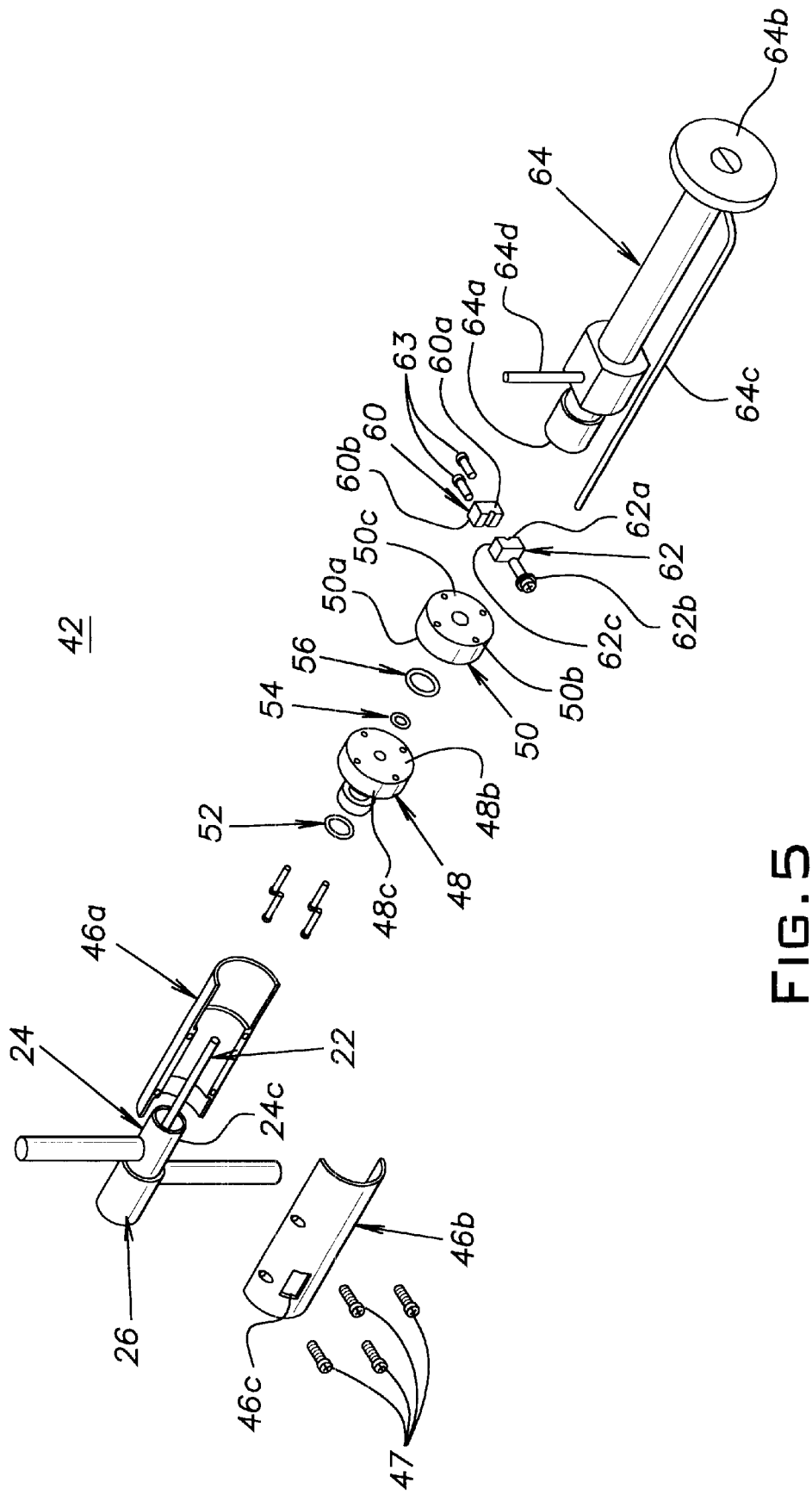
FIG. 5 shows an exploded perspective of the hardware elements of FIG. 3 which are used to connect the module to the injection valve.
Figure 6:
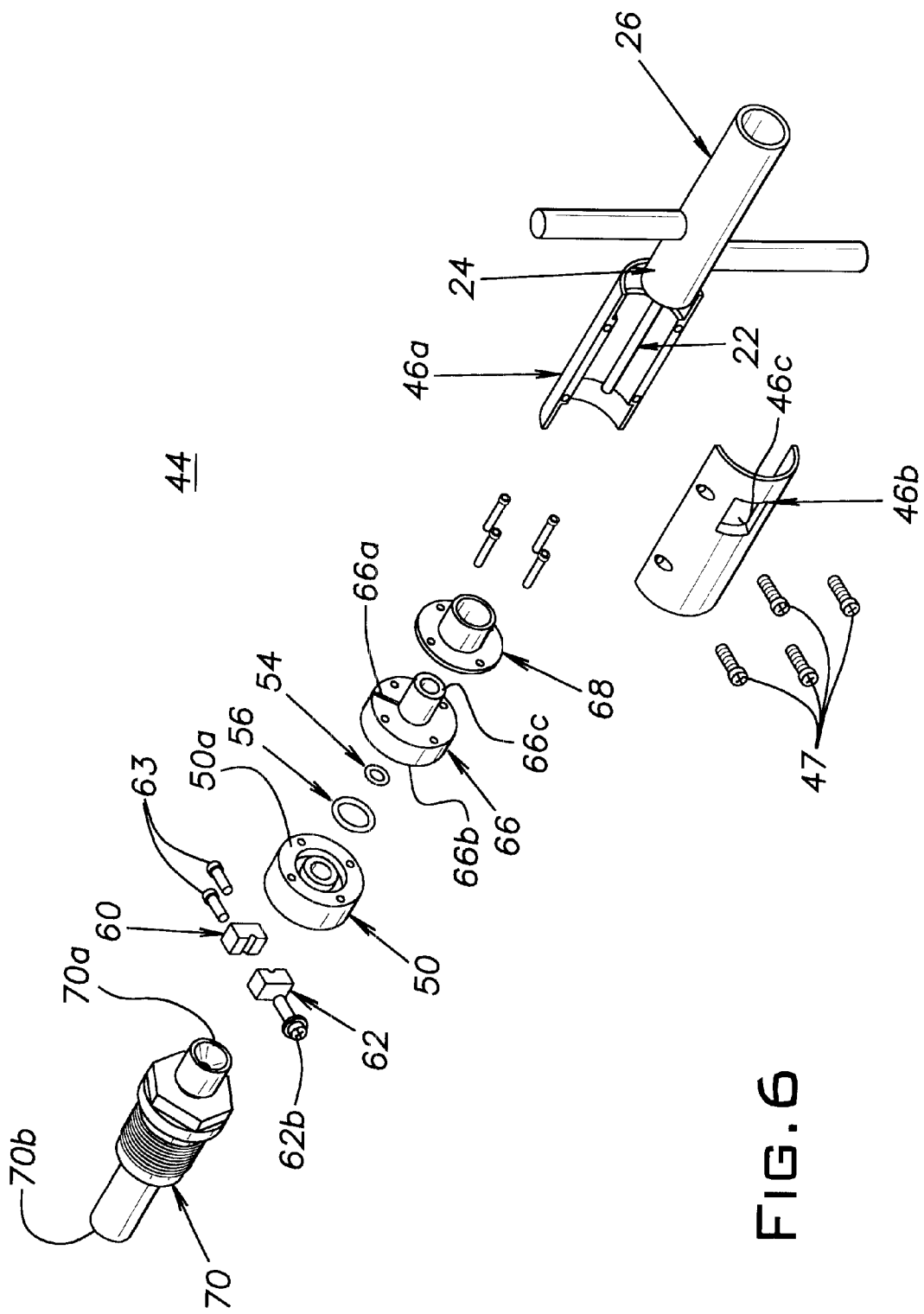
FIG. 6 shows an exploded perspective of the hardware elements of FIG. 3 which are used to connect the module to the flame ionization detector.

Referring now to FIG. 3 there is shown the micropacked column 22 inside of first and second jacket tubes 24, 26 along with an exploded perspective of the hardware elements collectively 42 that are used to connect the module 20 to the injection valve and the hardware elements collectively 44 that are used to connect the module 20 to flame ionization detector 7. An exploded perspective of the jacket tubes 24, 26 is shown in FIG. 4. An exploded perspective only of the hardware elements 42 that connect the module 20 to the valve 3 is shown in FIG. 5. An exploded perspective only of the hardware elements 44 that connect the module 20 to FID 7 is shown in FIG. 6. The jacket tubes 24, 26 and hardware elements 42 and 44 will now be described in connection with FIGS. 4–6.

As is shown in FIG. 4, the module 20 has an inner jacket tube 24 that slides into outer jacket tube 26. A stainless steel wire 23 is spiraled around the outside of the inner jacket 24. The wire 23 is tack welded on each revolution to the outside of inner jacket tube 24. The spiral wire 23 increases the turbulence and agitation of the air that flows around the outside of inner jacket tube 24 to thereby enhance the cooling of tube 24. When inner jacket tube 24 is slide into outer jacket tube 26 it has been found that the spiral wire 23 helps center tube 24 in tube 26. In addition the wire 23 is wrapped several times around each of the ends 24c, 24d of tube 24 to aid in plugging both ends of the tubes 24, 26 with solder, when the assembled tubes are soldered together.

Referring now to FIG. 5, there is shown an exploded perspective of hardware elements 42. Elements 42 include a heat shield 46 adjacent end 24c. The heat shield has first and second halves 46a and 46b which are, held together by the four screws 47. The first and second halves 46a and 46b each have four holes to accept an associated one of the four screws 47. The holes in half 46b are unthreaded and the holes in half 46a are threaded. Second half 46b has a window 46c whose function will be described below.

Figure 5A:
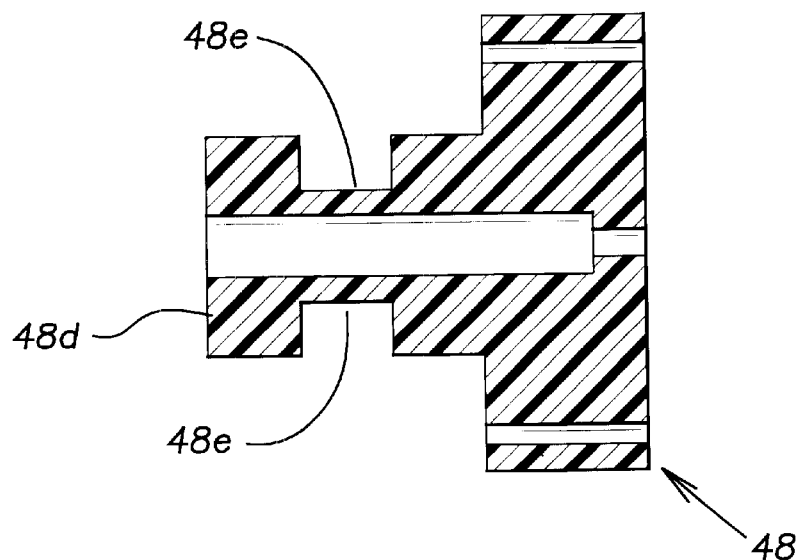
FIGS. 5a and 5b show close-ups of the bushings shown in FIG. 5.

The column 22 projects into the shield 46. Mounted on the column 22 at end 24c are a first bushing 48 followed by a second bushing 50. The first bushing 48 has an O-ring 52 which is between face 48a of bushing 48 and the end 24c. As can be in FIG. 5a, the bushing 48 has a projection 48d which projects outwardly toward end 24c when hardware elements 42 are assembled. Projection 48d has a circular groove 48e for accepting O-ring 52.

Figure 5B:
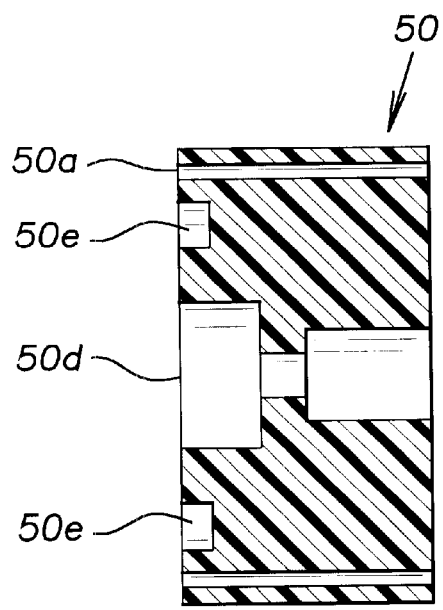

Between face 48b of bushing 48 and face 50a of bushing 50 are a small O-ring 54 and a large O-ring 56. As can be seen from FIG. 5b, face 50a of bushing 50 has a depression 50d for accepting O-ring 54 and a circular groove 50e for accepting O-ring 56. The assemblage of bushings 48 and 50 and O-rings 52, 54 and 56 are held together by screws 58. Each of bushings 48 and 50 have a center hole 48c and 50c, respectively and as can be appreciated from FIG. 5 the column 22 passes through the center holes 48c and 50c when hardware elements 42 are assembled.

Mounted adjacent face 50b of bushing 50 are first and second column blocks 60 and 62. Column blocks 60 and 62 are held together by screws 63 and the holes for screws 63 in block 60 are unthreaded whereas the holes for screws 63 in block 62 are threaded. As can be seen from FIG. 5, column blocks 60 and 62 each have a notch 60a and 62a in the associated face 60b and 62c. The notches 60a and 62a are parallel to the column 22 and the column 22 passes through the notches when the column blocks 60 and 62 are assembled.

The column blocks 60, 62 are used to provide the electrical power to column 22. To that end block 62 has a terminal 62b protruding outwardly therefrom. When hardware elements 42 are assembled, the terminal 62b protrudes through window 46c in heat shield 46b Hardware elements 42 also include a vaporizer 64 which is used to vaporize the sample from valve 3. Column 22 projects into end 64a of vaporizer 64 when hardware elements 42 are assembled. End 64b of vaporizer 64 is connected to valve 3. Vaporizer 64 also includes a first tube 64c which is the input for the carrier gas. Vaporizer 64 also includes a second tube 64d which is known as a splitter vent tube. As is well known to those in the art, only a small amount of the sample and carrier gas enters column 22. The remainder is vented through tube 64d.

Referring now to FIG. 6, there is shown an exploded perspective of hardware elements 44. Those of the elements 44 which are identical in form and function to an element in FIG. 5 have in FIG. 6 the same reference numeral that is used in FIG. 5 for that element. These identical elements will not be described again.

Figure 6A:
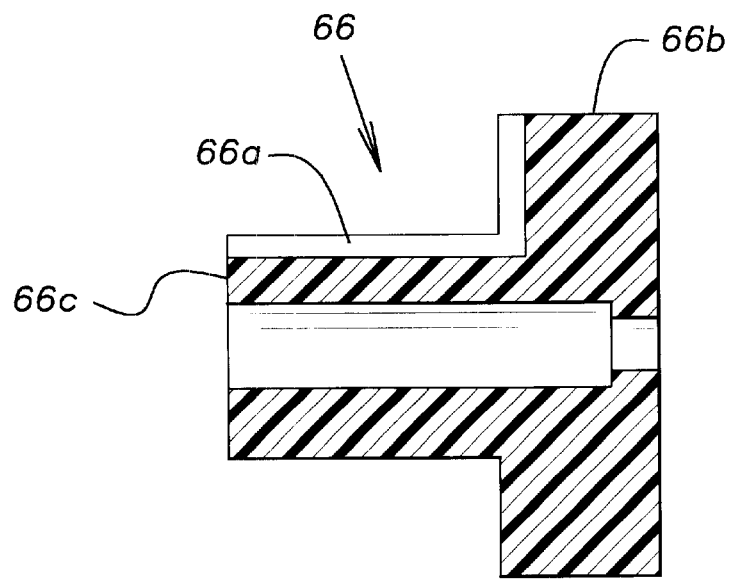
FIGS. 6a and 6b show close-ups of a bushing shown in FIG. 6 and of a adapter also shown in that figure.

Hardware elements 44 include a bushing 66. As can be seen in FIG. 6 and more clearly in FIG. 6a, bushing 66 has a slot 66a in circular portion 66b which extends through, projection 66c. A thermocouple (not shown) is inserted in slot 66a when hardware elements 44 are assembled. The slot 66a allows the thermocouple to be brought outside of the sealed environment which occurs when hardware elements 44 are assembled.

The thermocouple is welded to column 22. In one embodiment for module 30 a thermocouple is used that outputs 40 microvolts DC per one degree Celsius change in column 22 temperature. An AC voltage is used to heat column 22 and in that same embodiment the AC voltage used is ten volts. As those of ordinary skill in the art will appreciate the welding of the thermocouple to column 22 must be done with precision to avoid the influence on the thermocouple signal of the AC voltage used to heat column 22.

Figure 6B:
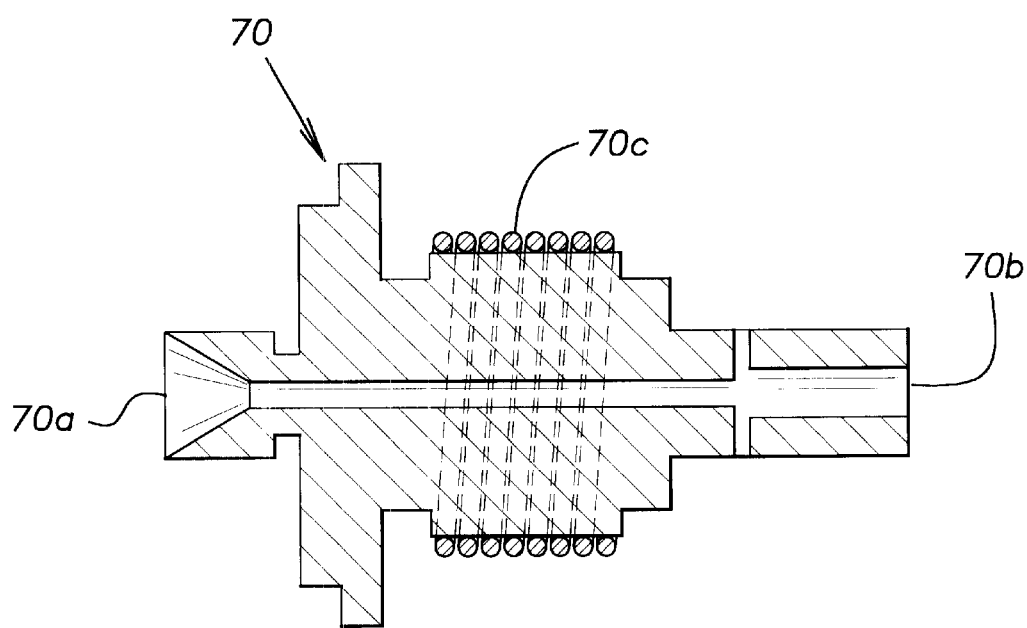

Hardware elements 44 also include a bushing cap 68. Hardware elements 44 also further includes between column blocks 60 and 62 and the FID 7 an adapter 70. End 70a of adapter 70 fits over column 22 and end 70b of adapter 70 is connected to FID 7. As is shown in FIG. 6b, adapter 70 includes a spring 70c. Adapter 70 provides a sliding fitting which in combination with spring 70c and a fixed fitting at the sample valve end of column 22 keep column 22 under tension as it is heated.

It should be appreciated that in use column 22 may be heated to about 320° C. while jacket tubes 24 and 26 are at the preheated temperature as was described in connection with FIG. 2. Thus the column 22 would bow and touch the tubing to thereby give temperature gradients. The sliding fitting of adapter 70 places the column under spring tension to prevent the bowing of the column.

The sliding fitting is provided by the hardware elements 44 when assembled in the following manner. As can be appreciated from FIG. 6 when hardware elements 44 are assembled, the heat shield halves 46a, 46b when grip the bushings 50, 66 and column blocks 60, 62 grip the column 22. The spring loading provided by spring 70c keeps the tension on the FID7 through the halves 46a, 46b and the bushings 50, 66. When hardware elements 44 are assembled the bushings 50, 66 pull on the column blocks 60, 62 which in turn keeps column 22 under tension. It should be appreciated that a similar gripping arrangement is also provided at the valve end of the column 22 by the hardware elements shown in FIG. 5. As the column 22 expands and contracts the bushings at the FID and valve ends of the column 22 slide in the tubing 24 and 26 that surrounds the column.

It is to be understood that the description of the preferred embodiment(s) is (are) intended to be only illustrative, rather than exhaustive, of the present invention. Those of ordinary skill will be able to make certain additions, deletions, and/or modifications to the embodiment(s) of the disclosed subject matter without departing from the spirit of the invention or its scope, as defined by the appended claims.

What is claimed is:

1. A temperature programmed module for use in a gas chromatograph comprising:

(a) a micropacked column through which a current can be passed to heat said column;
   (b) an inner jacket tube surrounding said column and having an outer diameter greater than the outer diameter of said column to define a space between said first jacket tube and said column; and
   (c) an outer jacket tube surrounding said inner jacket tube and having an outer diameter greater than said inner jacket tube outer diameter to define a space between said outer and said inner jacket tubes;

air having a controlled temperature flowing only into said space between said outer and said inner jacket tubes when it is desired to heat said column by passing said current through said column.

2. The module of claim 1 where said air having a controlled temperature flows into said space between said outer and said inner jacket tubes and into said space between said column and said inner jacket tube when said column is not heated.

3. The module of claim 1 wherein said inner and said outer jacket tubes both have an air inlet and an air outlet.

4. The module of claim 3 further comprising a heater for said air, said heater external to said column and said inner and outer jacket tubes and a temperature sensor adjacent said air inlet to said inner jacket tube for providing a signal to control said heater so that the temperature of said air is kept at a predetermined temperature.

5. The module of claim 1 further comprising means for directing the flow of air having a controlled temperature either into said space between said outer and said inner jacket tubes and also into said space between said inner jacket tube and said column or only into said space between said outer and inner jacket tubes.

6. The module of claim 1 further comprising a wire spiraled around the outer surface of said inner jacket tube.

7. The module of claim 6 wherein said wire is made from stainless steel and said wire is tack welded to said inner jacket tube outer surface on each revolution of said spiral.

8. The module of claim 1 further comprising a heater for said air, said heater external to said column and said inner and outer jacket tubes.

9. The module of claim 1 further comprising electrodes attached to said column for providing said heating current to said column.

10. The module of claim 1 further comprising means for providing tension to said column to accommodate thermal expansion of said column when said column is heated.

11. The module of claim 1 wherein said column has one end connected to a valve and the other end connected to a flame ionization detector and said module further comprises means for providing tension to said column to accommodate thermal expansion of said column when said column is heated.

12. The gas chromatograph of claim 11 wherein said means for providing tension to said column comprises a fitting connecting said column to said valve at said column one end, a sliding fitting connecting said column to said flame ionization detector at said column other end, said sliding fitting providing tension to said column by way of said flame ionization detector.

13. In a gas chromatograph, an enclosure whose temperature is not controlled, said enclosure comprising:

a temperature programmed module, said module comprising:

(a) a micropacked column through which a current can be passed to heat said column;
   (b) an inner jacket tube surrounding said column and having an outer diameter greater than the outer diameter of said column to define a space between said between said inner jacket tube and said column; and (c) an outer jacket tube surrounding said inner jacket tube and having an outer diameter greater than said inner jacket tube outer diameter to define a space between said outer and said inner jacket tubes;

air having a controlled temperature flowing only into said space between said outer and said inner jacket tubes when it is desired to heat said column by passing said current through said column.

14. The enclosure of claim 13 where in said module said air having a controlled temperature flows into said space between said outer and said inner jacket tubes and into said space between said column and said inner jacket tube when said column is not heated.

15. The enclosure of claim 14 where said air having a controlled temperature flowing into said space between said outer and said inner jacket tubes and into said space between said inner jacket tube and said column flows into to said enclosure.

16. The enclosure of claim 15 further comprising a sample injection valve and a flame ionization detector.

17. The enclosure of claim 13 where in said module said air having a controlled temperature flows only into said space between said outer and said inner jacket tubes when it is desired to heat said column also flows into to said enclosure.

18. The enclosure of claim 17 further comprising a sample injection valve and a flame ionization detector.

19. The gas chromatograph of claim 13 wherein said module further comprises means for providing tension to said column to accommodate thermal expansion of said column when said column is heated.

20. The gas chromatograph of claim 13 wherein said column has one end connected to a valve and the other end connected to a flame ionization detector and said module further comprises means for providing tension to said column to accommodate thermal expansion of said column when said column is heated.

21. The gas chromatograph of claims 20 wherein said means for providing tension to said column comprises a fitting connecting said column to said valve at said column one end, a sliding fitting connecting said column to said flame ionization detector at said column other end, said sliding fitting providing tension to said column by way of said flame ionization detector.

22. A method for assembling a temperature module having a micropacked column comprising the steps of:

(a) surrounding said column with a first jacket tube having an outer diameter greater than the outer diameter of said column to define a space between said first jacket tube and said column;

(b) surrounding said first jacket tube with a second jacket tube having an outer diameter greater than said first jacket tube outer diameter to define a space between said first and said second jacket tubes; and (c) providing on the outer surface of said first jacket tube prior to surrounding said first jacket tube with said second jacket tube a means for centering said first jacket tube in said second jacket tube.

23. The method of claim 22 wherein said step of providing said centering means comprises the step of spiraling a wire around said first jacket tube outer surface.

24. The method of claim 23 further comprising the step of tack welding said spiral wire to said first jacket tube outer surface on each revolution of said spiral prior to the execution of said step of surrounding said first jacket tube with said, second jacket tube.

25. The method of claim 24 further comprising the step of wrapping one or more revolutions of said wire around each end of said first jacket tube before the execution of said step of surrounding said first jacket tube with said second jacket tub.

26. The method of claim 22 wherein said column has first and second ends that project from said first jacket tube when said column is surrounded by said first jacket tube and said method includes the further step of attaching electrodes for providing said heating current to said first and second ends.

27. The method of claim 22 further comprising the step of providing tension to said column to accommodate thermal expansion of said column when said column is heated.

28. A method for using a temperature module having a micropacked column through which a current can be passed to heat said column, said column surrounded by an inner jacket tube having an outer diameter which is greater than the outer diameter of said column to define a space between said column and said inner jacket tube and an outer jacket surrounding said inner jacket tube said outer jacket having an outer diameter greater than said inner jacket tube outer diameter to define a space between said outer and said inner jacket tubes comprising the step of:

flowing air having a controlled temperature only into said space between said outer and said inner jacket tubes when it is desired to heat said column by passing said current through said column.

29. The method of claim 28 further comprising the step of directing said flowing air having said controlled temperature into said space between outer and said inner jacket tubes and into said space between said inner jacket tube and said column when it said column is not heated.

30. The method of claim 28 further comprising the step of heating said air by a heater which is external to said column and said inner and said outer jacket tubes.

31. The method of claim 28 further comprising the step of providing tension to said column to accommodate thermal expansion of said column when said column is heated.

32. A gas chromatograph comprising:

(a) a sample injector valve;

(b) a flame ionization detector; and (c) a temperature programmed module connected between said sample injector valve and said flame ionization detector, said module comprising:

(i) a micropacked column through which a current can be passed to heat said column;

(ii) an inner jacket tube surrounding said column and having an outer diameter greater than the outer diameter of said column to define a space between said first jacket tube and said column; and (iii) an outer jacket tube surrounding said inner jacket tube and having an outer diameter greater than said inner jacket tube outer diameter to define a space between said outer and said inner jacket tubes;

air having a controlled temperature flowing only into said space between said outer and said inner jacket tubes when it is desired to heat the column.

33. The gas chromatograph of claim 32 wherein said module further comprises means for providing tension to said column to accommodate thermal expansion of said column when said column is heated.

34. The gas chromatograph of claim 32 wherein said column has one end connected to said valve and the other end connected to said flame ionization detector and said module further comprises means for providing tension to said column to accommodate thermal expansion of said column when said column is heated.

35. The gas chromatograph of claim 34 wherein said means for providing tension to said column comprises a fitting connecting said column to said valve at said column one end, a sliding fitting connecting said column to said flame ionization detector at said column other end, said sliding fitting providing tension to said column by way of said flame ionization detector.

* * * * *